(12) United States Patent
Kobayashi et al.

(10) Patent No.: US 7,663,008 B2
(45) Date of Patent: Feb. 16, 2010

(54) METHOD OF CATALYTIC REACTION USING MICRO-REACTOR

(75) Inventors: Shu Kobayashi, Tokyo (JP); Yuichiro Mori, Tokyo (JP); Takehiko Kitamori, Tokyo (JP); Masaharu Ueno, Tokyo (JP); Kuniaki Okamoto, Saitama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 421 days.

(21) Appl. No.: 10/587,895

(22) PCT Filed: Jan. 26, 2005

(86) PCT No.: PCT/JP2005/001434

§ 371 (c)(1), (2), (4) Date: Jul. 28, 2006

(87) PCT Pub. No.: WO2005/073151

PCT Pub. Date: Aug. 11, 2005

(65) Prior Publication Data

US 2007/0161834 A1    Jul. 12, 2007

(30) Foreign Application Priority Data

Jan. 30, 2004  (JP) .............................. 2004-024373

(51) Int. Cl.
C07C 5/52  (2006.01)
C10G 45/00  (2006.01)

(52) U.S. Cl. .................. 585/275; 208/143; 422/100

(58) Field of Classification Search .................. 585/266, 585/250, 275; 208/143; 422/100
See application file for complete search history.

(56) References Cited

U.S. PATENT DOCUMENTS

2004/0028804 A1*  2/2004  Anderson et al. .......... 427/2.11
2005/0170142 A1*  8/2005  Remy ......................... 428/141

FOREIGN PATENT DOCUMENTS

WO  WO 99/22857 A1  5/1999

OTHER PUBLICATIONS

Notification of Transmittal of Copies of Translation of the International Preliminary Report on Patentability (Form PCT/IB/338) of International Application No. PCT/JP2005/001434 mailed Nov. 9, 2006 with Form PCT/ IPEA/409.

(Continued)

*Primary Examiner*—Walter D Griffin
*Assistant Examiner*—Renee Robinson
(74) *Attorney, Agent, or Firm*—Westerman, Hattori, Daniels & Adrian, LLP

(57) ABSTRACT

A method of catalytic reaction uses a micro-reactor (1) with a metal catalyst (5) or a metal complex catalyst (5) as a solid phase supported on the inner wall (4c) of a channel (4), a solution (7) dissolving a reactant as a liquid phase and hydrogen (9) as a gas phase are flown through the channel (4) in pipe flow state, and the reaction of the solution (7) and the gas (9) accelerated by the metal catalyst (5) or the metal complex catalyst (5) is conducted by three phase catalytic reaction of solid-liquid-gas phases. The metal catalyst (5) or the metal complex catalyst (5) is incorporated in a polymer, and hydrogenation reaction by three phase catalytic reductive reaction of a substance to be reduced can be conducted in short time at good yield. For hydrogenation reaction of unsaturated organics, the rate of reaction and yield are high when palladium catalyst is used, and carbonylation reaction can be conducted if carbon monoxide is used instead of hydrogen.

20 Claims, 8 Drawing Sheets

OTHER PUBLICATIONS

J. Kiji et al.; "A Convenient Route to β,γ-Unsaturated Esters without Formation of the ά,β-Isomer. Palladium-Catalyzed Alkoxycarbonylation of Allylic Halides under Alcohol-Potassium Carbonate Tow-Phase Condtions"; Bull. Chem. Soc. Jpn., vol. 69, pp. 1029-1031, 1996. Cited in ISR.

Ryo Akiyama et al.; "The Polymer Incarcerated Method for the Preparation of Highly Active Heterogeneous Palladium Catalysts"; J. Am. Chem. Soc., vol. 125, pp. 3412-3413, 2003. Cited in ISR (March).

Shokubai Kogaku Koza 6, "Shokubai Hanno (1) Suisanka", Chijinshokan Co., Ltd., Feb. 10, 1965, p. 224; 4.1.2 Suisanka Hanno ni Shiyosuru Shokubai. Cited in ISR.

"Sesshoku Suisanka Hanno—Yuki gosei eno Oyo-", Kabushiki Kaisha Tokyo Kagaku Dojin, Apr. 10, 1987, p. 41; 1.4 Sen'I Kinzoku Sakutai Shokubai no Chosei, p. 46, 1.4.4. Palldium Sakutai. Cited in ISR.

J. Kobayashi et al.; "A Microfluidic Device for Conducting Gas-Liquid-Solid Hydrogenation Reactions"; Science, vol. 304, No. 5675, pp. 1305-1308, 2004. Cited in ISR, (May).

R. S. Besser et al.; "Hydrocarbon hydrogenation and dehydrogenation reactions in microfabricated catalytic reactors"; Chemical Engineering Science, vol. 58, pp. 19-26, 2003. Cited in the Spec.

K. Jähnisch et al.; "Direct fluorination of toluene using elemental fluorine in gas/liquid microreactors"; Journal of Fluorine Chemistry, vol. 105, pp. 117-128, 2000. Cited in the Spec.

R. D. Chambers et al.; "Microreactors for elemental fluorine"; Chem. Comm., pp. 883-884, 1999. Cited in the Spec.

M. W. Losey et al.; "Microfabricated Multiphase Packed-Bed Reactors: Characterization of Mass Transfer and Reactions", Ind. Eng. Chem. Res., vol. 40, pp. 2555-2562, 2001. Cited in the Spec., (May).

Ryo Akiyama et al.; "The Polymer Incarcerated Method for the Preparation of Highly Active Heterogeneous Palladium Catalysts"; JACS Communications, J. Am. Chem. Soc., vol. 125, pp. 3412-3413; 2003. Cited in the Spec.

* cited by examiner

FIG. 1
(a)
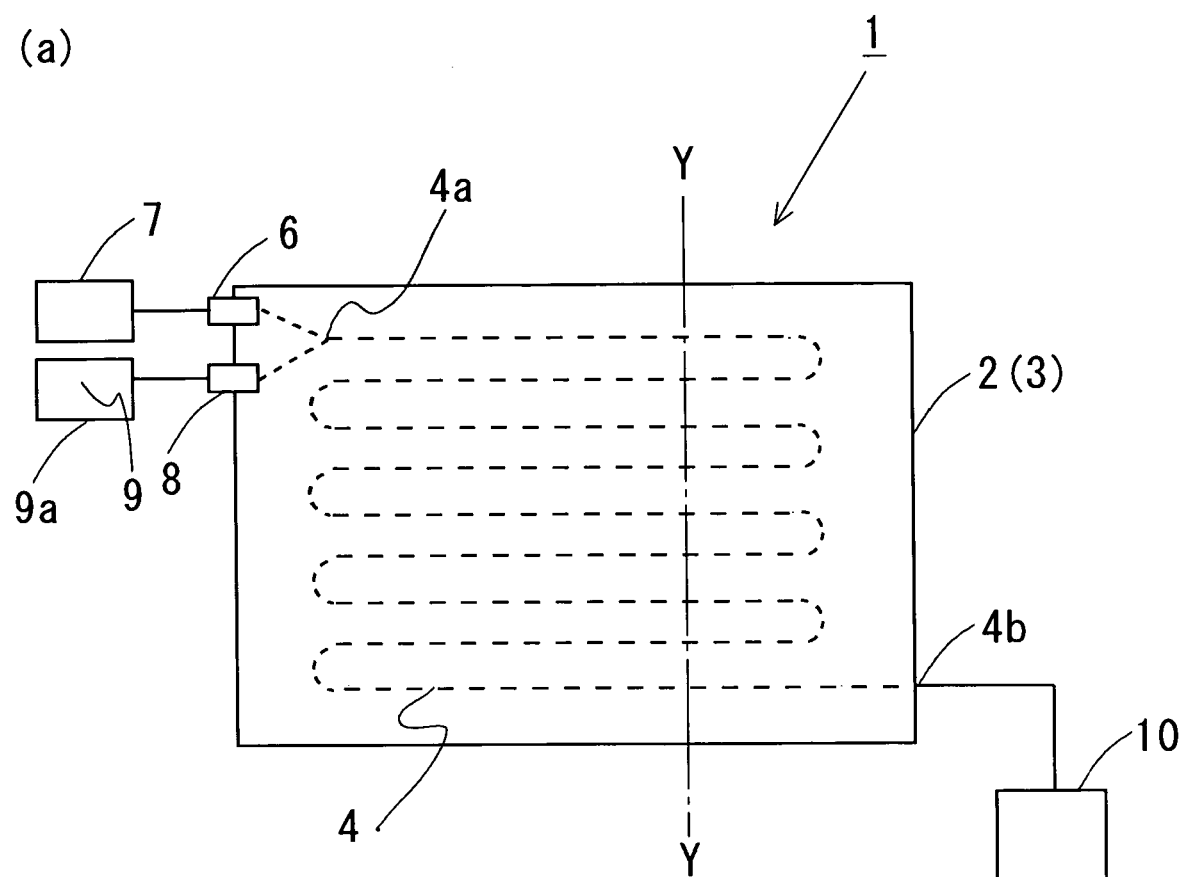
(b)
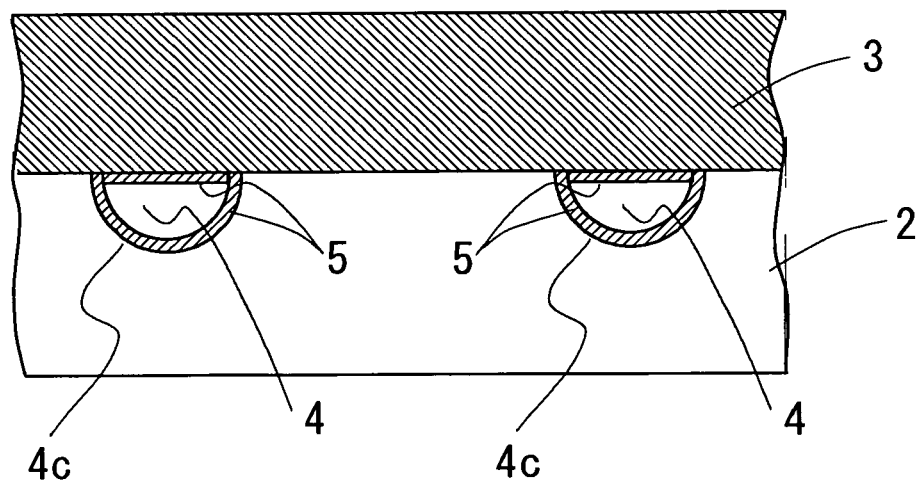

FIG. 6

| Example | Substance to be Reduced | Reaction Product | Yield(%) |
|---|---|---|---|
| | PI Palladium Catalyst-Immobilized Micro-Reactor, $H_2$ (1cm$^3$/min) THF, Room Temperature, within 5 mimutes | | |
| 2 | cyclohexenone | cyclohexanone | 100 |
| 3 | Ph-C(=CH$_2$)-CH$_2$-C(CH$_3$)$_2$-Ph | Ph-CH(CH$_3$)-CH$_2$-C(CH$_3$)$_2$-Ph | 100 |
| 4 | Ph-CH=CH-CH=CH-Ph | Ph-CH$_2$CH$_2$CH$_2$CH$_2$-Ph | 100 |
| 5 | Ph-C≡C-Ph | Ph-CH$_2$-CH$_2$-Ph | 100 |
| 6 | Ph-C≡C-CH$_2$OH | Ph-CH$_2$CH$_2$CH$_2$OH | 100 |
| 7 | 1-phenylcyclohexene | phenylcyclohexane | 99 |
| 8 | Ph-NO$_2$ | Ph-NH$_2$ | 82 |

FIG. 8
(a)
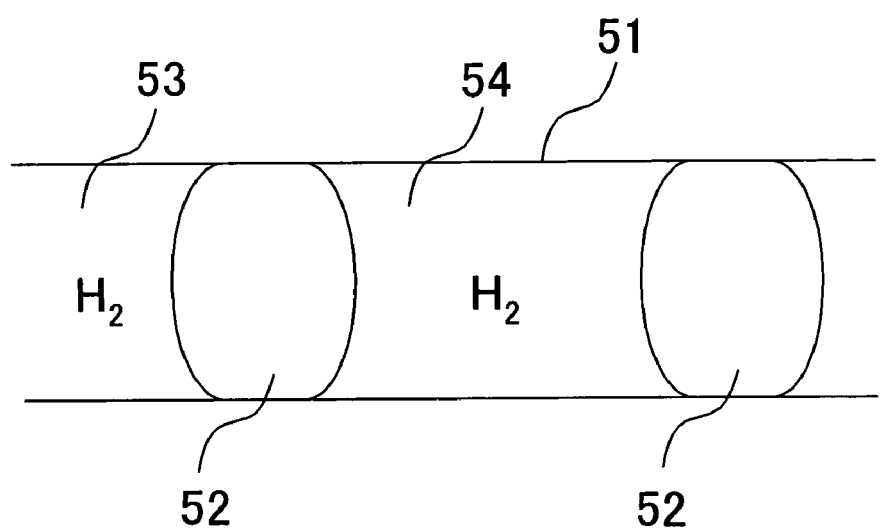
(b)
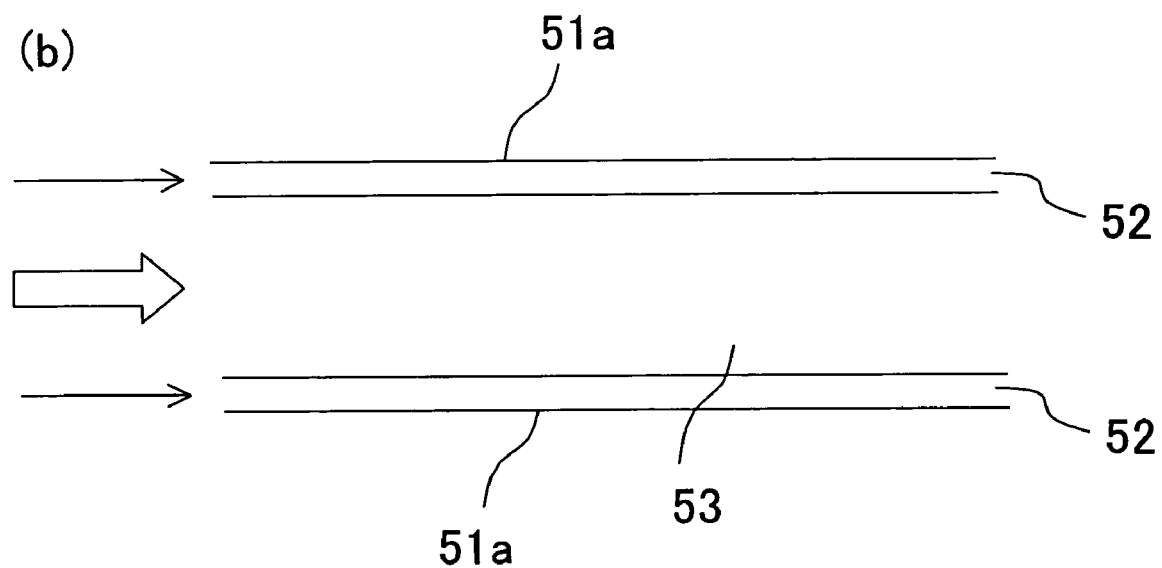

METHOD OF CATALYTIC REACTION USING MICRO-REACTOR

TECHNICAL FIELD

The present invention relates to a method of catalytic reaction using a micro-reactor.

BACKGROUND ART

The catalytic hydrogenation reaction using a heterogeneous catalyst, so-called catalytic reductive reaction is one of the most important processes in chemical industry, and is widely utilized for hydrogenation of aromatic nitro compounds and unsaturated bonds or de-benzylation reaction by hydrogenation, but there are often deterioration of yield and slow-down of reaction proceedings. Since these problems are solved by increasing the contact area between each phase, the catalytic surface (solid phase)-solution (liquid phase)-hydrogen gas (gas phase) (hereinafter, to be called a solid-liquid-gas phase reaction or three phase catalytic reduction reaction), such techniques have been tried as vigorous stirring or blowing in hydrogen gas as fine bubbles.

In the catalytic hydrogenation reaction in an ordinary reactor (hereinafter, properly called a flask reaction), ignition or explosion may be possible since hydrogen gas, solvent vapor, and highly active metal catalysts co-exist is the system.

On the other hand, organic syntheses using a micro-reactor have been rapidly developing. A micro-reactor is a generic term for a micro-reactor having micro-channels of the size of several to several hundred μm in an inactive material such as glass. Since a micro-reactor is small, strict temperature control is easily possible. Therefore, synthetic reactions using a micro-reactor have such merits as (1) high reaction efficiency on interfaces, (2) efficient mixing by molecular diffusion, and (3) easy temperature control, owing to large surface area per unit volume.

Thus, since synthetic reactions using a micro-reactor are faster in reaction time than those using ordinary reactors, and use a minute amount of reactants, the cost is low and they have been drawing attention as the reactors to develop novel compounds and medicines.

In Reference 1 in the list shown below, a hydrogenation reaction using a micro-reactor is described, which is a two-phase reaction of gas-solid with a catalyst imreferencemobilized on the inner wall of a micro-channel.

As the methods to pass liquid and gas as reactants through the micro-channels of a micro-reactor, a slug flow and a pipe flow are known. FIG. 8 is a cross-sectional view diagrammatically illustrating (a) slug flow and (b) pipe flow in a conventional micro-channel. As is shown in FIG. 8(a), a slug flow is the state of liquid 52 and gas 53 alternatively passing through a micro-channel 51 provided on a glass substrate. Also, as is shown in FIG. 8(b), as a pipe flow, gas 53 passes in the center part of a micro-channel 51, and liquid 52 passes between the gas 53 and the inner wall 51a of a micro-channel. Which type, a slug or a pipe flow, the fluid in a micro-channel takes can be controlled by adjusting the flow rates of liquid 52 and gas 53 passing through a micro-channel 51.

The reactions by a slug flow in a micro-channel 51 are described in the References listed below. Reference 2 below describes fluorination reaction by a two phase reaction with gas-liquid phases. The reactions by a pipe flow in a micro-channel are mentioned in the References listed below. Reference 3 below describes fluorination reaction by two phase system reaction with gas-liquid phases.

Carbon monoxide insertion reaction is reported as a reaction in a flask (refer to Reference 6.), but there is no reference for carbon monoxide insertion reaction using a micro-channel reactor.

Reference 1: R. S. Besser, and two others, Chem. Eng. Sci., Vol. 58, p. 19 (2003)

Reference 2: K. Jahnisch, et al., J. Fluorine Chem., Vol. 105, p. 117 (2000)

Reference 3: R. D. Chambers and R. C. H. Spink, Chem. Commun. 883 (1999)

Reference 4 M. W. Losey, and two others, Chem. md. Eng. Chem. Res., Vol. 40, p. 2555 (2001)

Reference 5: R. Akiyama and S. Kobayashi, J. Am. Chem. Soc., Vol. 125, pp. 3412 3413 (2003)

Reference 6: J. Kiji, T. Okano, Y. Higashimae, and Y. Fukui, Bull. Chem. Soc. Jpan., Vol. 69, pp. 1029 1031 (1996)

However, such three phase catalytic reactions as three phase catalytic reductive reactions of solid-liquid-gas phases using a heterogeneous catalyst have never so far been effectively realized by a micro-reactor.

DISCLOSURE OF THE INVENTION

In view of the problems mentioned above, it is an object of the present invention to provide a method of catalytic reaction using a micro-reactor capable of conducting three phase catalytic reaction of solid-liquid gas phases in short time at high yield.

In order to attain the above-mentioned object, the present invention is a method of catalytic reaction using a micro-reactor with a metal catalyst or a metal complex catalyst supported as a solid phase on the inner wall of a channel, characterized in that the metal catalyst or the metal complex catalyst is a catalyst incorporated in a polymer, said catalyst incorporated in a polymer is supported on the inner wall of a channel by covalent bond of a group provided on the inner wall of a channel or in a spacer via a group of the polymer surface, a gas as a gas phase is passed at the center part of the channel, a solution as a liquid phase in which a reactant is dissolved is passed between the gas and the catalyst supported on the inner wall of a channel, thereby the reaction of the solution and the gas is conducted by the three phase catalytic reaction of solid-liquid-gas phases accelerated by the metal catalyst or the metal complex catalyst. In the above-described aspect, the gas phase preferably consists of hydrogen or carbon monoxide.

Also, another aspect of the present invention is a method of catalytic reductive reaction using a micro-reactor with a metal or a metal complex catalyst supported as a solid phase on the inner wall of a channel, characterized in that the metal catalyst or the metal complex catalyst is a catalyst incorporated in a polymer, said catalyst incorporated in a polymer is supported on the inner wall of a channel by covalent bond of a group provided on the inner wall of a channel or in a spacer via a group of the polymer surface, hydrogen as a gas phase is passed at the center part of the channel, a solution as a liquid phase in which a reactant is dissolved is passed between hydrogen and the catalyst supported on the inner wall of a channel, thereby the reaction of the solution and hydrogen is conducted by the three phase catalytic reaction of solid-liquid-gas phases accelerated by the metal catalyst or the metal complex catalyst. According to the above-described aspect, hydrogenation reaction, hydrocracking reaction, or carbon monoxide insertion reaction of various substances can be conducted by three phase catalytic reaction in short time at high yield.

In the above-described aspect, the metal catalyst is preferably palladium. The metal complex catalyst is preferably a palladium complex catalyst.

The metal catalyst may be either chromium, manganese, iron, cobalt, nickel, copper, molybdenum, ruthenium, rhodium, tungsten, osmium, iridium, or platinum. The metal complex catalyst may be a metal complex catalyst of either chromium, manganese, iron, cobalt, nickel, copper, molybdenum, ruthenium, rhodium, tungsten, osmium, iridium, or platinum. The surface of the inner wall of a channel preferably has silanol groups, and the spacers are covalent bonded with silanol groups by Si—O—Si bond. The groups on a polymer surface is preferably epoxide groups, and the groups in the spacers are modified with functional groups bondable with epoxide groups.

According to the present invention, three phase catalytic reductive reaction can be conducted in short time by supporting a catalyst, particularly a metal or a metal complex catalyst as a solid phase on the inner wall of a micro-channel of a micro-reactor. Further, since such complicated operation as separation of products and a catalyst and recovery of a catalyst is unnecessary, continuous operation of long time is possible.

BRIEF DESCRIPTION OF THE DRAWINGS

FIG. 1 diagrammatically illustrates the makeup of a micro-reactor used in the embodiments of the present invention, and (a) is a plan view and (b) is a cross-sectional view along a line Y-Y.

FIG. 6 is a view illustrating the yields of hydrogenation reaction of Examples 2-8.

FIG. 8 is a cross-sectional view diagrammatically illustrating (a) a slug flow and (b) a pipe flow in a conventional micro-channel.

BEST MODES FOR CARRYING OUT THE INVENTION

Figure 2:
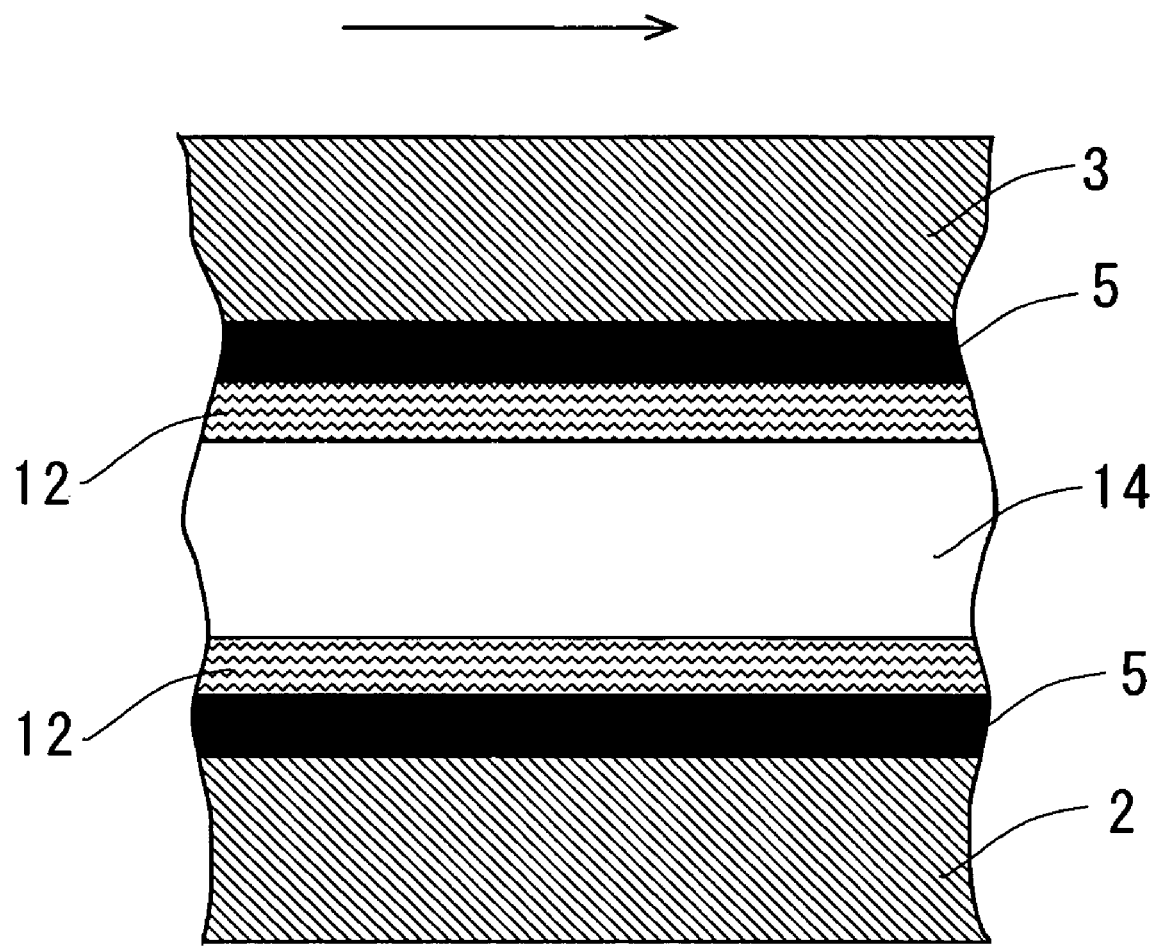
FIG. 2 is a cross-sectional view illustrating the states of a solution and hydrogen passing through a micro-channel of the micro-reactor used in the present invention.

Hereinafter, forms of implementations of the present invention will be better understood with reference to the accompanying drawings illustrating the invention described in detail below and several of its embodiments. Here, the various Examples illustrated in the accompanying drawings are in no way intended to specify or limit the present invention, but only to facilitate explanation and understanding of the present invention.

The present invention will be explained in detail below based on the forms of implementations illustrated in the figures.

FIG. 1 diagrammatically illustrates the makeup of a micro-reactor used in the embodiments of the present invention, and (a) is a plan view and (b) is a partial cross-sectional view along a line Y-Y. A micro-reactor 1 is provided with substrates 2 and 3 made of an inactive material such as glass, micro-channels 4 provided snakingly on the substrate 2, a catalyst 5 immobilized, that is, supported on the surface of the micro-channel 4, a solution 7 in which reactants are dissolved supplied via a liquid-feeding pump 6, a gas cylinder 9a supplying a gas 9 supplied via a gas valve 8, and a vessel for recovery 10. Here, hydrogen or carbon monoxide (CO) is mentioned as the gas supplied via a gas valve 8. Hereinafter, explanation will be made with hydrogen as the gas 9.

The micro-channel 4 is made with its cross-section carved in oblong or semi-circular shape by grinding with a tool such as an end mill or by etching with a mask. As is shown in FIG. 1(b), the substrate 2 on which the micro-channel 4 is provided is tightly fixed with a substrate 3 of the same size on which a micro-channel is not carved face to face so that the solution 7 and hydrogen 9 do not leach. The substrate 2 on which a micro-channel 4 is carved and the substrate 3 facing thereto may be of a material not corrosive by reactants or organic solvents, and may be of such a material as resins and metals in addition to glass.

The solution 7 is connected with the liquid-feeding pump 6 and Teflon (registered trademark) tube, and its supply rate is controlled by a flow rate adjuster using a syringe pump or others (not shown). Similarly, the hydrogen gas cylinder 9a is connected with the gas valve 8 and Teflon (registered trademark) tube, and its supply rate is controlled by a flow rate adjuster using a mass flow controller or others (not shown). The solution 7 and hydrogen 9 are combined at an inlet part 4a of the micro-channel. The vessel for recovery 10 is connected to an outlet part 4b of the micro-channel with Teflon (registered trademark) tube or others.

FIG. 2 is a cross-sectional view illustrating the states of a solution and hydrogen passing through a micro-channel of the present invention. As shown, hydrogen 14 passing through a micro-channel passes through a center part of the micro-channel 4. The solution 12 passing through a micro-channel passes between hydrogen 14 passes through a micro-channel and a catalyst supported on an inner wall 4c of the micro-channel in a so-called pipe flow state, from the inlet part 4a to the outlet part 4b. In this case, the flow rates of the solution 7 and hydrogen 9 are controlled to be in the above-mentioned pipe flow state by the flow rate adjusters not shown of the solution 7 and hydrogen 9.

In order to conduct solid-liquid-gas phase reaction using such a micro-reactor 1, a liquid reactant 7 from a liquid-feeding pump 6 and hydrogen 9 from a gas valve 8 are injected into a micro-channel 4 so to be in a pipe flow. While passing through the micro-channel 4, the reactant solution 12 and hydrogen 14 passing through the micro-channel are reacted by the action of a catalyst 5 supported on its inner wall 4c. The reaction mixture containing the object formed by reaction is collected into a vessel for recovery 10, and taken out upon necessity.

Here in the solid-liquid-gas phase reaction, hydrogenation of the reactant, that is, catalytic reductive reaction in case of hydrogen as the gas phase, and such catalytic reactions as carbon monoxide insertion reaction into the reactant, for example, carbonylation reaction in case of carbon monoxide as the gas phase can be caused.

As the solid catalyst 5 used for the solid-liquid-gas phase reaction, a metal or a metal complex catalyst of either of palladium (Pd), Chromium (Cr), manganese (Mn), iron (Fe), cobalt (Co), nickel (Ni), copper (Cu), molybdenum (Mo), ruthenium (Ru), rhodium (Rh), tungsten (W), osmium (Os), iridium (Ir), or platinum (Pt) may be used.

The above-mentioned catalyst 5 is preferably a polymer-inclusion catalyst (hereinafter to be called a PI catalyst) with the above-mentioned metal catalyst or metal complex catalyst immobilized in a polymer (Refer to the above-mentioned Reference 5.). In order to firmly fix the PI catalyst 5 not to dissociate from the inner wall 4c of the micro-channel, it is preferred to immobilize, that is, to support by a covalent bond. For that, in case that the inner wall 4c of the micro-channel is glass, one end of a spacer 4d of the PI catalyst 5 mentioned below is modified with a trialcoxysilane structure, and bonded to a silanol group on the glass surface as the inner wall 4c of the micro-channel. The other end of the spacer 4d can be bonded directly to, for example, an epoxy group on the polymer surface of the PI catalyst 5 by modifying it with a functional group such as amino acid group and others. In case that the inner wall 4c of the micro-channel is a resin, bonding is similarly possible to the above-mentioned epoxy group by modifying the resin surface with a functional group such as amino acid group and others.

Since thereby the PI catalyst can be firmly supported on the inner wall 4c of a micro-channel, it does not dissociate from the inner wall 4c of a micro-channel, and can be used repeatedly.

Explanation is next made of an example of the method to support the PI catalyst 5.

Figure 3:
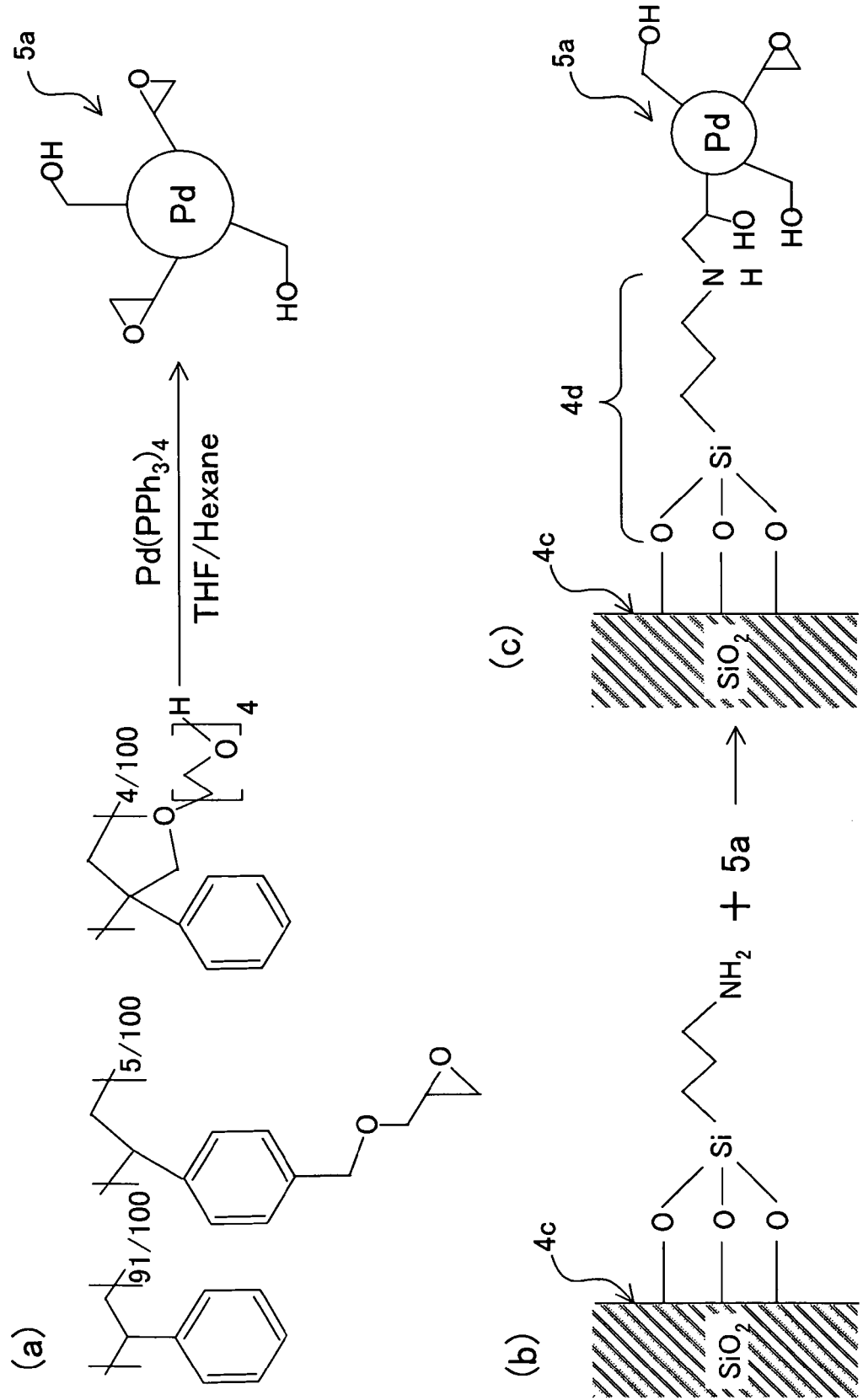
FIG. 3 is a view diagrammatically illustrating the reaction to support a PI catalyst in a micro-channel.

FIG. 3 is a view diagrammatically illustrating the reaction to support a PI catalyst 5 in a micro-channel 4. As is illustrated, the catalyst is micro-encapsulated by dissolving a polymer in an appropriate solvent and further adding a substance containing the catalyst (See FIG. 3(a).). In said microencapsulated catalyst 5a, the metal or the metal complex is present not only inside the capsule but also on or near the surface.

Next, it is bonded to the inner wall 4c modified with a spacer having an amino group by passing the solution containing the micro-encapsulated catalyst 5 through a microchannel, and heating (See FIG. 3(b).). FIG. 3(c) diagrammatically illustrates the inner wall of a micro-channel on which is supported the thus obtained PI catalyst 5, and 4d illustrates the spacer of the surface group of a micro-channel and the catalyst.

According to the method of three phase catalytic reaction of the present invention, hydrogenation reaction can be conducted in short time by three phase catalytic reaction in so-called pipe flow state in which the solution 7 containing reactants is flown contacting the inner wall 4c of the micro-channel on which the catalyst is supported, and hydrogen 9 flows at the center part of the micro-channel 4.

In case that gas 9 is carbon monoxide, carbon monoxide insertion reaction can be conducted in short time by three phase catalytic reaction in so-called pipe flow state in which carbon monoxide 9 flows at the center part of the micro-channel 4. As such a carbon monoxide insertion reaction, organic carbonylation reaction and others may be mentioned. In this case, since a metal catalyst 5 is supported on the micro-channel inner wall 4c, the recovery and regeneration work of, for example, valuable palladium catalyst is unnecessary, and further since it is the reaction in a micro-reactor 1, the amounts to be used of the reactants, solvents, and hydrogen 9 used for the reaction are so remarkably decreased that the cost is reduced.

Since also the scale up of a reactor apparatus is easy only by arranging a number of micro-reactors 1 in parallel, the desired products can be obtained easily, quickly, and in the necessary amount, the feed-stock consumption, required time and space are low, and the products can be obtained in such a pure form that separation and refining are not necessary.

Therefore, according to the method of three phase catalytic reaction of the present invention, it is the reaction method quite suitable to development of medicine and its manufacturing process. It is also preferred for green chemistry (environment-oriented chemistry).

Explanation is next made of the examples of the present invention.

EXAMPLE 1

Using a micro-reactor 1 of FIG. 1, hydrogenation of benzalacetone as a substance to be reduced was conducted. As the micro-reactor, a glass plate 2 of size 3 cm×7 cm having a micro-channel 4 of length 45 cm was used. The cross-sectional shape of the micro-channel 4 was 200 μm wide and 100 μm deep semi-circular. On the inner wall 4c of the micro-channel was immobilized polymer-inclusion palladium (hereinafter to be called PI palladium) containing palladium fixed on polymer (See FIGS. 3(b) and (c).).

Figure 4:
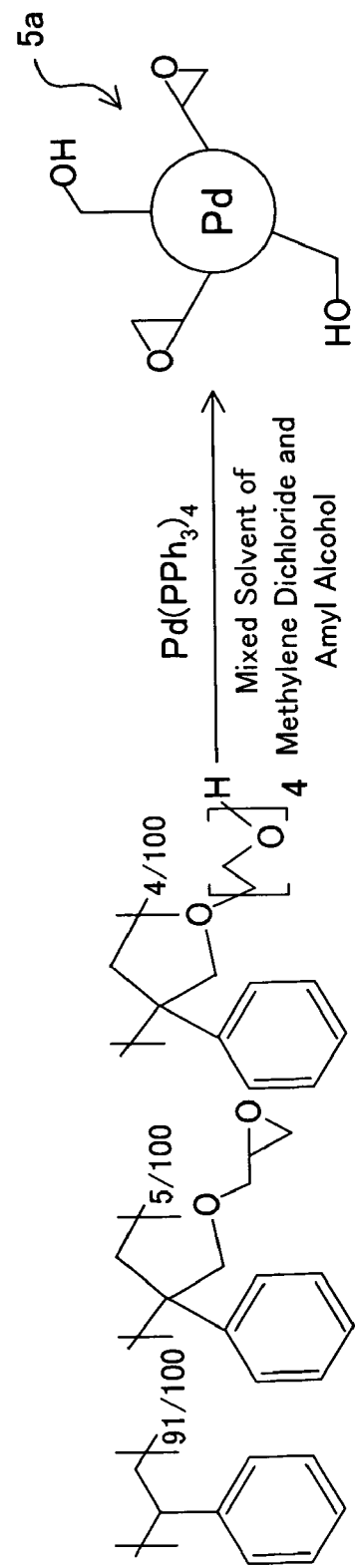
FIG. 4 is a view illustrating the method of preparing the PI palladium catalyst used in Example 1.

FIG. 4 is a view illustrating the method of preparing the PI palladium catalyst used in Example 1. As is illustrated, the micro-encapsulated PI palladium catalyst 5a was prepared by using three kinds of monomers, by bridging reaction mixing the polymer made up in their ratio 91:5:4 with tetrakis(triphenylphosphin) palladium in a solvent mixture of methylene dichloride and amyl alcohol, and heating at about 150° C.

Into a micro-channel 4, THF (tetrahydrofuran) solution 7 of benzalacetone as a substance to be reduced (concentration 0.1 mole %/1000 $cm^3$) and hydrogen gas were supplied at flow rates 0.1 $cm^3$/hour and 1 $cm^3$/minute, respectively, the substance to be reduced and hydrogen 9 were passed through the micro-channel 4 in pipe flow state, thereby hydrogenation reaction of benzalacetone was conducted. The reaction was conducted at room temperature.

Figure 5:
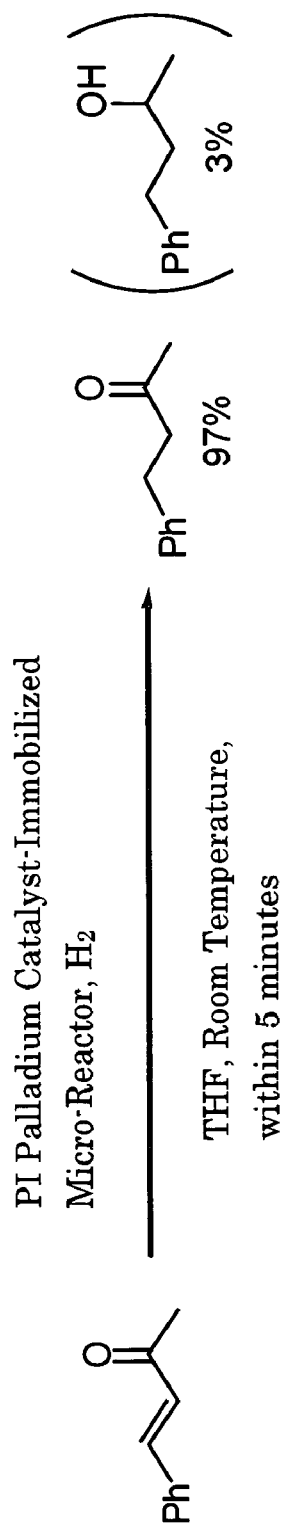
FIG. 5 is a view illustrating the reaction products from hydrogenation reaction of benzalacetone of Example 1.

Next, the reaction product was analyzed by NMR using proton (nuclear magnetic resonance apparatus, hereinafter to be called $^1$H-NMR). FIG. 5 is a view illustrating the reaction products from hydrogenation reaction of benzalacetone of Example 1. As is obvious from the figure, 4-phenyl-2-butanone and 4-phenyl-2-butanol were obtained by hydrogenation of benzalacetone within five minutes as reaction time at the yield of 97% and 3%, respectively.

The hydrogenation reaction time of Example 1 was calculated as about five minutes from the whole volume of the micro-channel 4 and the volume flow rate of liquid phase, and its observed value was two minutes. This value of reaction time is about 1/30 compared with about one hour as the ordinary flask reaction.

EXAMPLE 2

In Example 2, hydrogenation reaction was conducted under the same condition as Example 1 for THF diluted solution concentration of the substance to be reduced, its flow rate, and hydrogen 9 flow rate, using cyclohexen-2-one as the substance to be reduced. The reaction time was within five minutes. The reaction product was analyzed by $^1$H-NMR.

FIG. 6 is a view illustrating the yields of hydrogenation reaction of Example 2. As is obvious from the figure, the analytical result of the reaction product by $^1$H-NMR showed almost complete hydrogenation of cyclohexen-2-one, and cyclohexanone was obtained at about 100% yield.

EXAMPLE 3

In Example 3, hydrogenation reaction was conducted under the same condition as Example 1 for THF diluted solution concentration of the substance to be reduced, its flow rate, and hydrogen 9 flow rate, using 2,4-diphenyl-4-methyl- 1-pentene as the substance to be reduced. The reaction time was within five minutes. The analytical result of the reaction product by $^1$H-NMR showed almost complete hydrogenation of 2,4-diphenyl-4-methyl-1-pentene, and 2,4-diphenyl-2-methylpentane was obtained at about 100% yield (See FIG. 6.).

EXAMPLE 4

In Example 4, hydrogenation reaction was conducted under the same condition as Example 1 for THF diluted solution concentration of the substance to be reduced, its flow rate, and hydrogen 9 flow rate, using 1,4-diphenyl-1,3-butadiene as the substance to be reduced. The reaction time was within five minutes. The analytical result of the reaction product by $^1$H-NMR showed almost complete hydrogenation of 1,4-diphenyl-1,3-butadiene, and 1,4-diphenylbutane was obtained at about 100% yield (See FIG. 6.).

EXAMPLE 5

In Example 5, hydrogenation reaction was conducted under the same condition as Example 1 for THF diluted solution concentration of the substance to be reduced, its flow rate, and hydrogen 9 flow rate, using 1,2-diphenylacetylene as the substance to be reduced. The reaction time was within five minutes. The analytical result of the reaction product by $^1$H-NMR showed almost complete hydrogenation of 1,2-diphenylacetylene, and 1,2-diphenylethane was obtained at about 100% yield (See FIG. 6.).

EXAMPLE 6

In Example 6, hydrogenation reaction was conducted under the same condition as Example 1 for THF diluted solution concentration of the substance to be reduced, its flow rate, and hydrogen 9 flow rate, using 3-phenyl-2-propin-1-ol as the substance to be reduced. The reaction time was within five minutes. The analytical result of the reaction product by $^1$H-NMR showed almost complete hydrogenation of 3-phenyl-2-propin-1-ol, and 3-phenyl-1-propanol was obtained at about 100% yield (See FIG. 6.).

EXAMPLE 7

In Example 7, hydrogenation reaction was conducted under the same condition as Example 1 for THF diluted solution concentration of the substance to be reduced, its flow rate, and hydrogen 9 flow rate, using 1-phenylcyclohexene as the substance to be reduced. The reaction time was within five minutes. The analytical result of the reaction product by $^1$H-NMR showed almost complete hydrogenation of 1-phenylcyclohexene, and phenylcyclohexane was obtained at 99% yield (See FIG. 6.).

EXAMPLE 8

In Example 8, nitrobenzene was used as the substance to be reduced. Hydrogenation reaction of nitrobenzene was conducted by supplying ethanol diluted solution 7 of the substance to be reduced (concentration was 0.1 mole %/1000 cm$^3$) and hydrogen gas at flow rates 0.1 cm$^3$/hour and 1 cm$^3$/minute, respectively, and passing the substance to be reduced and hydrogen 9 through the micro-channel 4 in pipe flow state. Other conditions were same as Example 1, and the reaction time was within five minutes. The reaction was conducted at room temperature. The analytical result of the reaction product by a gas chromatography apparatus showed hydrogenation of nitrobenzene, and aniline was obtained at 82% yield (See FIG. 6.).

EXAMPLE 9

In Example 9, carbon monoxide insertion reaction was conducted using cinnamyl chloride as the reactant. The used catalyst was same as Example 1. Basic ethanol diluted solution (sodium salt of p-nitrophenol) of cinnamyl chloride was used. The concentrations of cinnamyl chloride and sodium salt of p-nitrophenol were 0.125 mole %/1000 cm$^3$ and 0.188 mole %/1000 cm$^3$, respectively.

Next, the solution 7 containing said cinnamyl chloride as the reactant and carbon monoxide gas 9 were supplied at flow rates 0.1 cm$^3$/hour and 2 cm$^3$/minute, respectively. By passing the reactant and carbon monoxide through the micro-channel 4 in pipe flow state, carbon monoxide insertion reaction, that is, cabonylation of cinnamyl chloride was conducted, and ethyl ester of 4-phenyl-3-butenoic acid was obtained. The reaction time was within five minutes. The reaction was conducted at room temperature.

Figure 7:
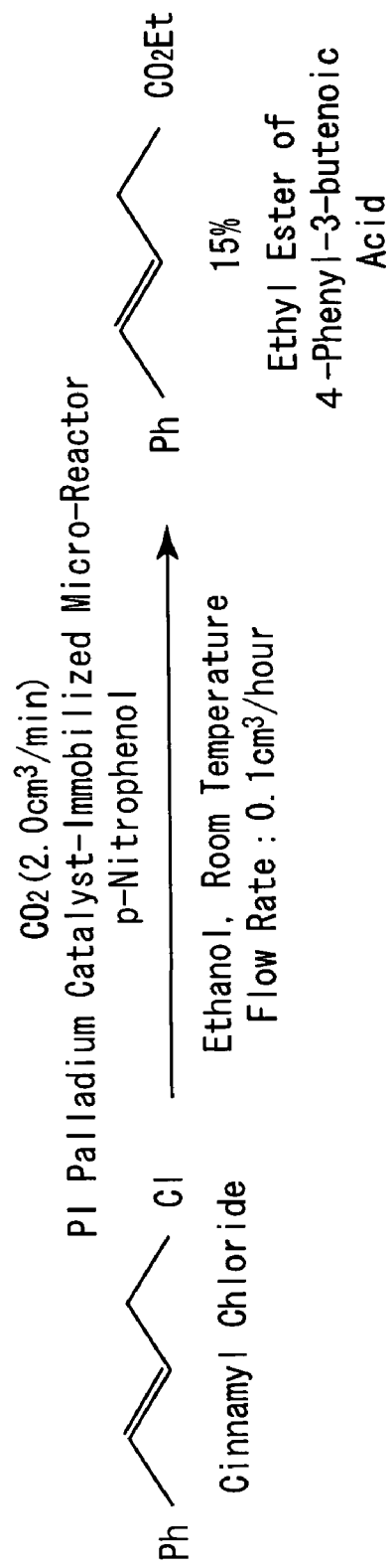
FIG. 7 is a view illustrating the yield of carbonylation reaction of Example 9.

FIG. 7 is a view illustrating the yield of carbonylation reaction of Example 9. As is shown in the figure, the analytical result of the reaction product by a gas chromatography apparatus showed carbonylation of cinnamyl chloride, and ethyl ester of 4-phenyl-3-butenoic acid was obtained at 15% yield. Carbon monoxide insertion reaction has low reaction rate in general, and needs high temperature and high pressure in many cases. However, in the reaction of Example 9, though the yield in a micro-channel reactor was not impressive 15% at present, the acceleration of the reaction is considered to be taking place sufficiently, taking into account the reaction condition at room temperature and ordinary pressure, and within five minutes of reaction time. Therefore, since it is three phase reaction of solid-liquid-gas phases as in hydrogenation reaction, the reaction is considered to proceed more efficiently in a micro-channel compared with that in a flask. Thereby, the reaction rate is considered to be remarkably improved by pipe flow as reaction system.

INDUSTRIAL APPLICABILITY

In accordance with the method of catalytic reaction using a micro-reactor of the present invention, reaction of hydrogenation of a substance to be reduced and others can be conducted in short time and at good yield. Also in the method of catalytic reaction using a micro-reactor of the present invention, since the consumption of materials of the reactant and gas and power consumption required for their supply and stirring are extremely low, the cost is low compared with the reactions using the conventional reactors. Therefore, three phase catalytic reductive reaction an others needed for the search for medicines and fine chemicals can be conducted at low cost.

What is claimed is:

1. A method of catalytic reaction using a micro-reactor, characterized in that:
    said method of catalytic reaction uses a micro-reactor with
        a metal catalyst or a metal complex catalyst as a solid phase supported on an inner wall of a channel, characterized in that
    said metal catalyst or said metal complex catalyst is a catalyst incorporated in a polymer,
    said catalyst incorporated in a polymer is supported on the inner wall of said channel by covalent bond to a group provided on the inner wall of said channel or said catalyst incorporated in a polymer is supported on the inner wall of said channel by covalent bond via a spacer bonded to a group of the polymer surface,
said group provided on the inner wall of said channel is an amino group, and
said amino group is covalent bonded with said group of said polymer surface or said spacer,
a gas as a gas phase is passed at the center part of the channel,
a solution as a liquid phase in which a reactant is dissolved is passed between said gas and said catalyst supported on the inner wall of said channel,
thereby the reaction of said solution and said gas is conducted by the three phase catalytic reaction of solid-liquid-gas phases accelerated by said metal catalyst or said metal complex catalyst.

2. The method of catalytic reaction using a micro-reactor as set forth in claim 1, characterized in that said metal catalyst is palladium.

3. The method of catalytic reaction using a micro-reactor as set forth in claim 1, characterized in that said metal catalyst is either one of chromium, manganese, iron, cobalt, nickel, copper, molybdenum, ruthenium, rhodium, tungsten, osmium, iridium, and palladium.

4. The method of catalytic reaction using a micro-reactor as set forth in claim 1, characterized in that said metal complex catalyst is a palladium complex catalyst.

5. The method of catalytic reaction using a micro-reactor as set forth in claim 1, characterized in that said metal complex catalyst is a metal complex catalyst of either one of chromium, manganese, iron, cobalt, nickel, copper, molybdenum, ruthenium, rhodium, tungsten, osmium, iridium, and palladium.

6. The method of catalytic reaction using a micro-reactor as set forth in claim 1, characterized in that said gas phase consists of hydrogen or carbon monoxide.

7. A method of catalytic reaction using a micro-reactor, characterized in that:
said method of catalytic reaction uses a micro-reactor with a metal catalyst or a metal complex catalyst as a solid phase supported on an inner wall of a channel, characterized in that
said metal catalyst or said metal complex catalyst is a catalyst incorporated in a polymer,
said catalyst incorporated in a polymer is supported on the inner wall of said channel by covalent bond to a group provided on the inner wall of said channel or said catalyst incorporated in a polymer is supported on the inner wall of said channel by covalent bond via a spacer bonded to a group of the polymer surface,
said group provided on the inner wall of said channel is an amino group, and
said amino group is covalent bonded with acid group of said polymer surface or said spacer,
hydrogen as a gas phase is passed at the center part of the channel,
a solution as a liquid phase in which a reactant is dissolved is passed between said hydrogen and said catalyst supported on the inner wall of said channel,
thereby the reaction of said solution and said hydrogen is conducted by the three phase catalytic reaction of solid-liquid-gas phases accelerated by said metal catalyst or said metal complex catalyst.

8. The method of catalytic reaction using a micro-reactor as set forth in claim 7, characterized in that said metal catalyst is palladium.

9. The method of catalytic reaction using a micro-reactor as set forth in claim 7, characterized in that said metal catalyst is either one of chromium, manganese, iron, cobalt, nickel, copper, molybdenum, ruthenium, rhodium, tungsten, osmium, iridium, and palladium.

10. The method of catalytic reaction using a micro-reactor as set forth in claim 7, characterized in that said metal complex catalyst is a palladium complex catalyst.

11. The method of catalytic reaction using a micro-reactor as set forth in claim 7, characterized in that said metal complex catalyst is a metal complex catalyst of either one of chromium, manganese, iron, cobalt, nickel, copper, molybdenum, ruthenium, rhodium, tungsten, osmium, iridium, and palladium.

12. A method of catalytic reaction using a micro-reactor characterized in that:
said method of catalytic reaction uses a micro-reactor with a metal catalyst or a metal complex catalyst as a solid phase supported on an inner wall of a channel, characterized in that
said metal catalyst or said metal complex catalyst is a catalyst incorporated in a polymer,
said catalyst incorporated in a polymer is supported on the inner wall of said channel by covalent bond via a spacer bonded to a group of the polymer surface,
said surface of the inner wall of said channel has silanol groups, and said spacer is covalent bonded with said silanol group by Si—O—Si bond;
a gas as a gas phase is passed at the center part of the channel,
a solution as a liquid phase in which a reactant is dissolved is passed between said gas and said catalyst supported in the inner wall of said channel,
thereby the reaction of said solution and said gas is conducted by the three phase catalytic reaction of solid-liquid-gas phases accelerated by said metal catalyst or said metal complex catalyst.

13. The method of catalytic reaction using a micro-reactor as set forth in claim 12, characterized in that the group on said polymer surface is an epoxide group, and the group in said spacer is modified with a functional group bondable with an epoxide group.

14. The method of catalytic reaction using a micro-reactor as set forth in claim 12, characterized in that said metal catalyst is either one of chromium, manganese, iron, cobalt, nickel, copper, molybdenum, ruthenium, rhodium, tungsten, osmium, iridium, and palladium.

15. The method of catalytic reaction using a micro-reactor as set forth in claim 12, characterized in that said metal complex catalyst is a metal complex catalyst of either one of chromium, manganese, iron, cobalt, nickel, copper, molybdenum, ruthenium, rhodium, tungsten, osmium, iridium, and palladium.

16. The method of catalytic reaction using a micro-reactor as set forth in claim 12, characterized in that said gas phase consists of hydrogen or carbon monoxide.

17. A method of catalytic reaction using a micro-reactor, characterized in that:
said method of catalytic reaction uses a micro-reactor with a metal catalyst or a metal complex catalyst as a solid phase supported on an inner wall of a channel, characterized in that
said metal catalyst or said metal complex catalyst is a catalyst incorporated in a polymer,
said catalyst incorporated in a polymer is supported on the inner wall of said channel by covalent bond via a spacer bond to a group of the polymer surface, said surface of the inner wall of said channel has silanol groups, and said spacer is covalent bonded with said silanol group by Si—O—Si bond;

hydrogen as a gas phase is passed at the center part of the channel, a solution as a liquid phase in which a reactant is dissolved is passed between said hydrogen and said catalyst supported on the inner wall of said channel, thereby the reaction of said solution and said hydrogen is conducted by the three phase catalytic reaction of solid-liquid-gas phases accelerated by said metal catalyst or said metal complex catalyst.

18. The method of catalytic reaction using a micro-reactor as set forth in claim 17, characterized in that the group on said polymer surface is an epoxide group, and the group in said spacer is modified with a functional group bondable with an epoxide group.

19. The method of catalytic reaction using a micro-reactor set forth in claim 17, characterized in that said metal catalyst is either one of chromium, manganese, iron, cobalt, nickel, copper, molybdenum, ruthenium, rhodium, tungsten, osmium, iridium, and palladium.

20. The method of catalytic reaction using a micro-reactor as set forth in claim 17, characterized in that said metal complex catalyst is a metal complex catalyst of either one of chromium, manganese, iron, cobalt, nickel, copper, molybdenum, ruthenium, rhodium, tungsten, osmium, iridium, and palladium.

* * * * *